United States Patent [19]

Hino et al.

[11] Patent Number: 5,358,965
[45] Date of Patent: Oct. 25, 1994

[54] HYDRAZONE DERIVATIVES, PROCESSES FOR PRODUCTION THEREOF, AND USES THEREOF

[75] Inventors: Tomokazu Hino, Ibaraki; Nobuharu Andoh, Osaka; Hiroshi Hamaguchi, Kyoto; Atsushi Kanaoka, Kawachinagano, all of Japan

[73] Assignee: Nihon Nohyaku Co., Ltd., Japan

[21] Appl. No.: 68,204

[22] Filed: May 28, 1993

Related U.S. Application Data

[62] Division of Ser. No. 791,227, Nov. 13, 1991, Pat. No. 5,304,573.

[30] Foreign Application Priority Data

Nov. 17, 1990 [JP] Japan ................................. 2-312414
Nov. 30, 1990 [JP] Japan ................................. 2-334471

[51] Int. Cl.$^5$ ................ C07C 251/80; C07C 243/22; A01N 33/26; A01N 37/44
[52] U.S. Cl. .................................... 514/539; 514/522; 514/615; 558/414; 560/34; 564/149; 564/150
[58] Field of Search ................ 564/149, 150; 514/615, 514/539; 560/34

[56] References Cited

U.S. PATENT DOCUMENTS

| | | | |
|---|---|---|---|
| 3,641,098 | 2/1972 | Bachel et al. | 564/150 |
| 3,885,042 | 5/1975 | Mulder et al. | 514/590 |
| 4,140,795 | 2/1979 | Boger et al. | 558/413 X |
| 4,207,338 | 6/1980 | Eckhardt et al. | 514/538 |
| 4,331,680 | 5/1982 | Giles | 514/639 |
| 4,344,893 | 8/1982 | Copping | 558/53 |
| 4,394,387 | 7/1983 | Copping | 514/517 |
| 4,432,994 | 2/1984 | Giles | 514/482 |
| 4,983,755 | 1/1991 | Buhmann et al. | 560/24 |
| 5,112,382 | 5/1992 | Hsu | 558/414 X |

FOREIGN PATENT DOCUMENTS

| | | |
|---|---|---|
| 0254461 | 1/1988 | European Pat. Off. . |
| 2171217 | 9/1973 | France . |
| 48-91223 | 11/1973 | Japan . |
| 54-122261 | 9/1979 | Japan . |
| 56-45452 | 4/1981 | Japan . |
| 63-93761 | 4/1988 | Japan . |
| 2021110 | 11/1979 | United Kingdom . |
| 9206076 | 4/1992 | World Int. Prop. O. . |

*Primary Examiner*—Peter O'Sullivan
*Attorney, Agent, or Firm*—Cushman, Darby & Cushman

[57] ABSTRACT

The present invention relates to a hydrazone derivative represented by the general formula (I) shown below:

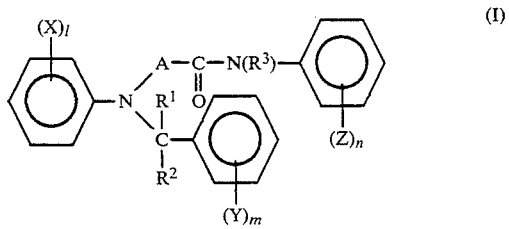

wherein the substituents are as defined in the specification, processes for preparing the derivative, and uses of the derivative as an insecticide.

The hydrazone derivative has a marked insecticidal effect on insect pests, especially against LEPIDOPTERA and COLEOPTERA.

13 Claims, No Drawings

HYDRAZONE DERIVATIVES, PROCESSES FOR PRODUCTION THEREOF, AND USES THEREOF

This is a division of application Ser. No 07/791,227, filed Nov. 13, 1991, now U.S. Pat. No. 5,304,573.

BACKGROUND OF THE INVENTION

1. Field of the Invention

The present invention relates to hydrazone derivatives, processes for production thereof, agricultural and horticultural insecticides, and uses thereof.

The hydrazone derivatives are represented by the general formula (I):

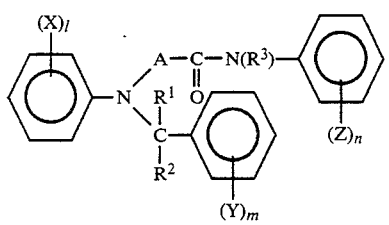

wherein each of $R^1$, $R^2$ and $R^3$ independently represents a hydrogen atom, or an alkyl group having 1 to 5 carbon atoms; A represents —N=C($R^4$)— or —N-H—CH($R^4$)— (wherein $R^4$ represents a hydrogen atom or an alkyl group having 1 to 5 carbon atoms); X, which may be the same or different, represents a halogen atom, nitro group, an alkyl group having 1 to 5 carbon atoms, a haloalkyl group having 1 to 5 carbon atoms, an alkoxy group having 1 to 5 carbons, an alkylthio group having 1 to 5 carbons, an alkylsulfinyl group having 1 to 5 carbons or an alkylsulfonyl group having 1 to 5 carbons; Y, which may be the same or different, represents a halogen atom, cyano group, nitro group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, an alkylsulfinyl group having 1 to 5 carbon atoms, an alkylsulfonyl group having 1 to 5 carbon atoms, a haloalkylthio group having 1 to 5 carbon atoms, a haloalkylsulfinyl group having 1 to 5 carbon atoms, a haloalkylsulfonyl group having 1 to 5 carbon atoms, an alkynyl group having 2 to 5 carbon atoms, or an alkoxycarbonyl group having 1 to 5 carbon atoms; Z, which may be the same or different, represents a halogen atom, nitro group, cyano group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, a haloalkylthio group having 1 to 5 carbon atoms, an alkylsulfinyl group having 1 to 5 carbon atoms, a haloalkylsulfinyl group having 1 to 5 carbon atoms, an alkylsulfonyl group having 1 to 5 carbon atoms, a haloalkylsulfonyl group having 1 to 5 carbon atoms, a haloalkylsulfonyloxy group having 1 to 5 carbons, an alkylcarbonyl group having 1 to 5 carbon atoms, or phenoxy group; l, m and n each represents 0 or an integer of 1 to 5; processes for preparation thereof, agricultural and horticultural insecticides and uses thereof.

2. Related Art Statement

Japanese Patent Application KOKAI (Laid-Open) Nos. 48-91223, 54-122261, 56-45452, 63-93761, etc. disclose hydrazones as insecticides and agents for controlling insect pests.

SUMMARY OF THE INVENTION

The present inventors earnestly investigated in order to develop a novel insecticide and consequently found that a hydrazone derivative represented by the general formula (I) shown below has neither been disclosed nor even suggested in the prior art, is a novel compound not found in any of publications and has an excellent insecticidal effect at a low dosage. The present invention has thus been accomplished.

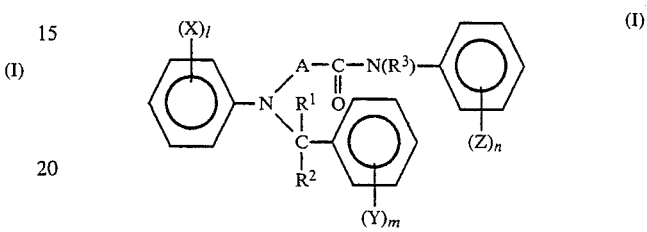

wherein X, Y, Z, $R^1$, $R^2$, $R^3$, l, m and n have the same significances as defined above.

That is, the present invention relates to the novel hydrazone derivative represented by the general formula (I) shown above, an insecticidal composition comprising the hydrazone derivative as an active ingredient, and a method for controlling agricultural and horticultural insect pests using the composition. The present invention also relates to processes for production of the hydrazone derivative.

DETAILED DESCRIPTION OF PREFERRED EMBODIMENTS

In the hydrazone derivatives represented by the general formula (I) described above, examples of $R^1$, $R^2$, $R^3$ and $R^4$ as substituents include hydrogen atom and an alkyl group such as methyl, ethyl, n-propyl, i-propyl, n-butyl, i-butyl, s-butyl, t-butyl, n-pentyl, i-pentyl, etc. Preferred examples are hydrogen atom and methyl group.

Examples of X include a halogen atom such as chlorine, bromine, iodine or fluorine; nitro group; an alkyl group such as methyl, ethyl, n-propyl, i-propyl, n-butyl, i-butyl, s-butyl, t-butyl, n-pentyl, i-pentyl, etc.; a haloalkyl group having 1 to 5 carbon atoms such as chloromethyl, dichloromethyl, trichloromethyl, bromomethyl, dibromomethyl, tribromomethyl, fluoromethyl, difluoromethyl, trifluoromethyl, chloroethyl, dichloroethyl, trichloroethyl, tetrachloroethyl, bromoethyl, dibromoethyl, tribromoethyl, tetrabromoethyl, fluoroethyl, difluoroethyl, trifluoroethyl, tetrafluoroethyl, chloropropyl, dichloropropyl, trichloropropyl, fluoropropyl, difluoropropyl, trifluoropropyl, chlorobutyl, dichlorobutyl, fluorobutyl, difluorobutyl, trifluorobutyl, fluoropentyl, etc.; an alkoxy group having 1 to 5 carbon atoms such as methoxy, ethoxy, n-propoxy, i-propoxy, n-butoxy, i-butoxy, s-butoxy, t-butoxy, n-pentyloxy, i-pentyloxy, etc.; an alkylthio group having 1 to 5 carbon atoms such as methylthio, ethylthio, n-propylthio, i-propylthio, n-butylthio, i-butylthio, s-butylthio, t-butylthio, n-pentylthio, i-pentylthio, etc.; an alkylsulfinyl group such as methylsulfinyl, ethylsulfinyl, n-propylsulfinyl, i-propylsulfinyl, n-butylsulfinyl, i-butylsulfinyl, s-butylsulfinyl, t-butylsulfinyl, n-pentylsulfinyl, i-pentylsulfinyl, etc.; and an alkylsulfonyl group such as methylsulfonyl, ethylsulfonyl, n-propylsulfonyl, i-propylsulfonyl, n-butylsulfonyl, i-butylsulfonyl, s-butylsulfonyl, t-butylsulfonyl, n-pentylsulfonyl, i-pentylsulfonyl, etc. Preferred examples are a halogen atom such as chlorine and a haloalkyl group such as trifluoromethyl group. These substituents are preferably substituted at the 3-position.

Examples of Y include a halogen atom such as chlorine, bromine, iodine or fluorine; cyano group, nitro group; an alkyl group, a haloalkyl group or an alkoxy group exemplified for X; a haloalkoxy group having 1 to 5 carbon atoms such as chloromethoxy, dichloromethoxy, trichloromethoxy, bromomethoxy, dibromomethoxy, tribromomethoxy, fluoromethoxy, difluoromethoxy, trifluoromethoxy, chloroethoxy, dichloroethoxy, trichloroethoxy, tetrachloroethoxy, bromoethoxy, dibromoethoxy, tribromoethoxy, tetrabromoethoxy, fluoroethoxy, difluoroethoxy, trifluoroethoxy, tetrafluoroethoxy, chloropropoxy, dichloropropoxy, trichloropropoxy, fluoropropoxy, difluoropropoxy, trifluoropropoxy, chlorobutoxy, dichlorobutoxy, fluorobutoxy, difluorobutoxy, trifluorobutoxy, fluoropentyloxy, etc.; an alkylthio group having 1 to 5 carbon atoms, an alkylsulfinyl group having 1 to 5 carbon atoms or an alkylsulfonyl group having 1 to 5 carbon atoms, exemplified for X; a haloalkylthio group having 1 to 5 carbon atoms such as chloromethylthio, dichloromethylthio, trichloromethylthio, bromomethylthio, dibromomethylthio, tribromomethylthio, fluoromethylthio, difluoromethylthio, trifluoromethylthio, chloroethylthio, dichloroethylthio, trichloroethylthio, tetrachloroethylthio, bromoethylthio, dibromoethylthio, tribromoethylthio, tetrabromomethylthio, fluoroethylthio, difluoroethylthio, trifluoroethylthio, tetrafluoroethylthio, chloropropylthio, dichloropropylthio, trichloropropylthio, fluoropropylthio, difluoropropylthio, trifluoropropylthio, chlorobutylthio, dichlorobutylthio, fluorobutylthio, difluorobutylthio, trifluorobutylthio, fluoropentylthio, etc.; a haloalkylsulfinyl group such as chloromethylsulfinyl, dichloromethylsulfinyl, trichloromethylsulfinyl, bromomethylsulfinyl, dibromomethylsulfinyl, tribromomethylsulfinyl, fluoromethylsulfinyl, difluoromethylsulfinyl, trifluoromethylsulfinyl, chloroethylsulfinyl, dichloroethylsulfinyl, trichloroethylsulfinyl, bromoethylsulfinyl, dibromoethylsulfinyl, tribromoethylsulfinyl, tetrabromoethylsulfinyl, fluoroethylsulfinyl, difluoroethylsulfinyl, trifluoroethylsulfinyl, tetrafluoroethylsulfinyl, chloropropylsulfinyl, dichloropropylsulfinyl, trichloropropylsulfinyl, fluoropropylsulfinyl, difluoropropylsulfinyl, trifluoropropylsulfinyl, chlorobutylsulfinyl, dichlorobutylsulfinyl, fluorobutylsulfinyl, difluorobutylsulfinyl, trifluorobutylsulfinyl, fluoropentylsulfinyl, etc.; a haloalkylsulfonyl group such as chloromethylsulfonyl, dichloromethylsulfonyl, trichloromethylsulfonyl, bromomethylsulfonyl, dibromomethylsulfonyl, tribromomethylsulfonyl, fluoromethylsulfonyl, difluoromethylsulfonyl, trifluoromethylsulfonyl, chloroethylsulfonyl, dichloroethylsulfonyl, trichloroethylsulfonyl, tetrachloroethylsulfonyl, bromoethylsulfonyl, dibromoethylsulfonyl, tribromoethylsulfonyl, tetrabromoethylsulfonyl, fluoroethylsulfonyl, difluoroethylsulfonyl, trifluoroethylsulfonyl, tetrafluoroethylsulfonyl, chloropropylsulfonyl, dichloropropylsulfonyl, trichloropropylsulfonyl, fluoropropylsulfonyl, difluoropropylsulfonyl, trifluoropropylsulfonyl, chlorobutylsulfonyl, dichlorobutylsulfonyl, fluorobutylsulfonyl, difluorobutylsulfonyl, trifluorobutylsulfonyl, fluoropentylsulfonyl, etc.; an alkynyl group such as ethynyl, 1-propynyl, 2-propynyl, 1-butynyl, 2-butynyl, 3-butynyl, 1-pentynyl, 2-pentynyl, 3-pentynyl, 4-pentynyl etc.; an alkoxycarbonyl group such as methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, n-pentyloxycarbonyl, i-pentyloxycarbonyl, etc. Preferred examples are nitro group, cyano group and difluoromethylsulfinyl group. These substituents are preferably substituted at the 4-position.

Examples of Z include a halogen atom, nitro group, cyano group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, a haloalkylthio group having 1 to 5 carbon atoms, an alkylsulfinyl group having 1 to 5 carbon atoms, an alkylsulfonyl group having 1 to 5 carbon atoms, a haloalkylsulfinyl group having 1 to 5 carbon atoms and a haloalkylsulfonyl group having 1 to 5 carbon atoms exemplified for Y; in addition thereto, an alkylcarbonyl group having 1 to 5 carbon atoms such as methylcarbonyl, ethylcarbonyl, n-propylcarbonyl, i-propylcarbonyl, n-butylcarbonyl, i-butylcarbonyl, s-butylcarbonyl, t-butylcarbonyl, n-pentylcarbonyl, etc.; a haloalkylsulfonyloxy group having 1 to 5 carbon atoms such as chloromethylsulfonyloxy, dichloromethylsulfonyloxy, trichloromethylsulfonyloxy, fluoromethylsulfonyloxy, difluoromethylsulfonyloxy, trifluoromethylsulfonyloxy, chloroethylsulfonyloxy, dichloroethylsulfonyloxy, trichloroethylsulfonyloxy, tetrachloroethylsulfonyloxy, fluoroethylsulfonyloxy, difluoroethylsulfonyloxy, trifluoroethylsulfonyloxy, tetrafluoroethylsulfonyloxy, chloropropylsulfonyloxy, dichloropropylsulfonyloxy, trichloropropylsulfonyloxy, tetrachloropropylsulfonyloxy, fluoropropylsulfonyloxy, difluoropropylsulfonyloxy, trifluoropropylsulfonyloxy, tetrafluoropropylsulfonyloxy, chlorobutylsulfonyloxy, chlorobutylsulfonyloxy, dichlorobutylsulfonyloxy, trichlorobutylsulfonyloxy, tetrachlorobutylsulfonyloxy, fluorobutylsulfonyloxy, difluorobutylsulfonyloxy, trifluorobutylsulfonyloxy, tetrafluorobutylsulfonyloxy, chloropentylsulfonyloxy, dichloropentylsulfonyloxy, fluoropentylsulfonyloxy, difluoropentylsulfonyloxy, etc.; or phenoxy group. Preferred examples are a halogen atom such as chlorine atom, fluorine atom, bromine atom or iodine atom; or a haloalkyl group such as trifluoromethyl group; and a haloalkoxy group such as trifluoromethoxy group. These substituents are preferably substituted at the 4-position.

Representative processes for preparing the hydrazone derivatives of the present invention represented by the general formula (I) are shown below.

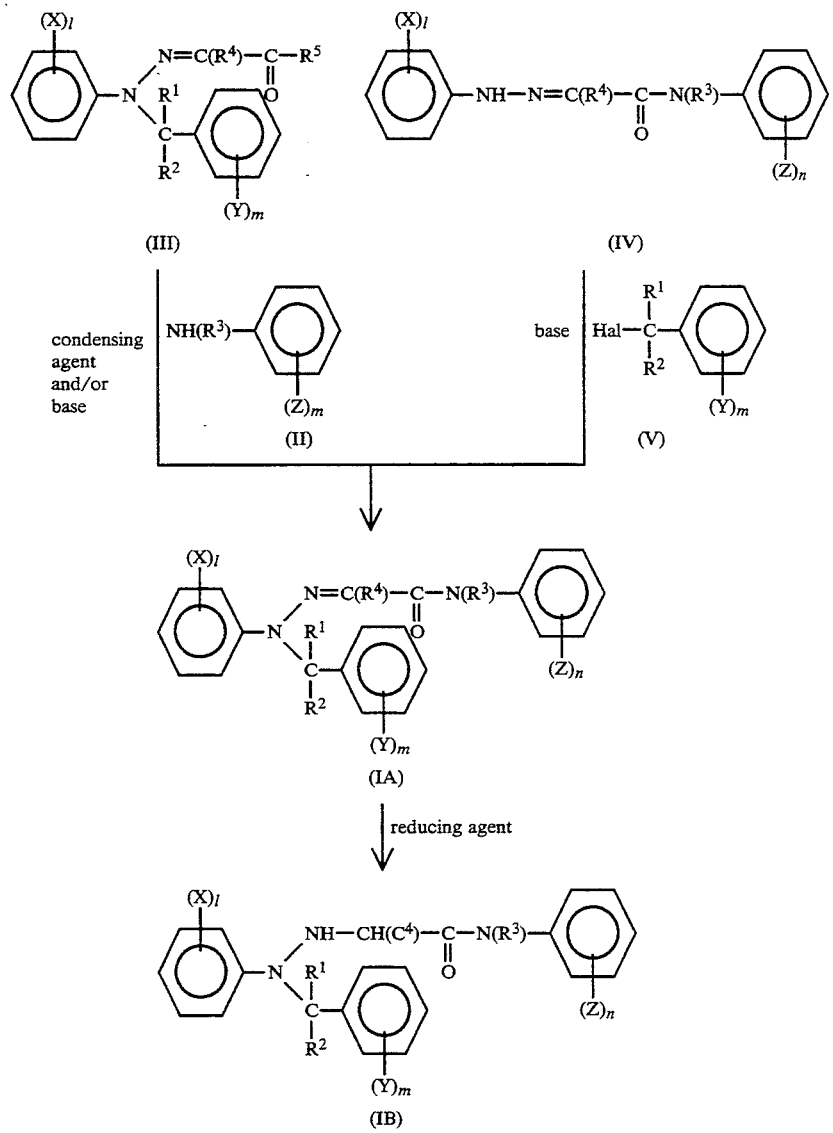

wherein X, Y, Z, $R^1$, $R^2$, $R^3$, $R^4$, l, m and n have the same significances as defined above and $R^5$ represents a halogen atom or hydroxy group.

Either by reacting compounds represented by the general formula (III) with anilines represented by the general formula (II) in an inert solvent in the presence or absence of a base or a condensing agent, or by reacting compounds represented by the general formula (IV) with halides represented by the general formula (V) in an inert solvent in the presence of a base, the hydrazone derivatives represented by the general formula (IA) are prepared. The hydrazone derivatives (IA) are subjected to reduction in the presence of a reducing agent to give the hydrazone derivatives represented by the general formula (IB).

The hydrazone derivatives represented by the general formulae (IA) and (IB) fall under the hydrazone derivatives represented by the general formula (I).

1. Process for preparing the compounds of general formula (IA) from the compounds of general formula (III)

As the inert solvent which can be used in this reaction, any solvent may be used so long as it does not markedly inhibit the progress of the reaction. There can be exemplified halogenated hydrocarbons such as dichloromethane, chloroform, carbon tetrachloride, etc.; nitriles such as acetonitrile, benzonitrile, etc.; linear ethers such as Methyl Cellosolve, diethyl ether, etc.; cyclic ethers such as dioxane, tetrahydrofuran, etc.; ketones such as acetone, methyl ethyl ketone, etc.; aromatic hydrocarbons such as benzene, toluene, xylene, etc.; esters such as ethylacetate, etc.; N,N-dimethylformamide (DMF), dimethylsulfoxide (DMSO), pyridine and the like. These inert solvents may be used singly or as a mixture thereof.

As the base which can be used in this reaction, an organic base or an inorganic base can be used. Examples of the inorganic base include hydroxides or carbonates of alkali metal atoms such as sodium, potassium, etc. and alkaline earth metal atoms such as calcium, magnesium, etc.; sodium hydride. Examples of the organic base include triethylamine, pyridine, N,N-dimethylaniline, 2,6-dimethylpyridine, 4-N,N-dimethylaminopyridine, etc. As to the amount of the base used, the base may be used in a catalytic amount or, in the range chosen from an equimolar amount or an excess amount based on the compounds represented by the general formula (III).

As the condensing agent, for example, carbodiimidazole, dicyclohexylcarbodiimide, 2-chloro-1- methylpyridinium iodide, etc. may be used. The condensing agent may be used within the amount chosen from the range of an equimolar amount to an excess molar amount, based on the compound represented by the general formula (III).

The reaction proceeds in an equimolar relation and it is thus sufficient to use the respective reactants in equimolar amounts. However, the anilines may be used in an excess amount.

The reaction temperature is properly chosen in the range from room temperature to the boiling point of the inert solvent used. The reaction is carried out preferably with heating.

Although the reaction time is varied depending on the degree of reaction, the reaction temperature and the like, it may be chosen in the range of several minutes to 48 hours.

After completion of the reaction, the desired compound is isolated from a reaction solution in a conventional manner such as removal of the solvent by distillation, solvent extraction, etc., and if necessary and desired, purified by recrystallization, column chromatography, etc., whereby the desired compound can be prepared.

2. Process for preparing the compounds of general formula (IA) from the compounds of general formula (IV)

The compound represented by the general formula (IV) is reacted with the halide represented by the general formula (V) in an inert solvent in the presence of a base to prepare the hydrazone derivative represented by the general formula (IA).

As the inert solvent which can be used in this reaction, any solvent may be used so long as it does not markedly inhibit the progress of the reaction. There can be exemplified alcohols such as methanol, ethanol, propanol, etc., halogenated hydrocarbons such as dichloromethane, chloroform, carbon tetrachloride, etc.; aromatic hydrocarbons such as benzene, toluene, xylene, etc.; nitriles such as acetonitrile, benzonitrile, etc.; linear ethers such as Methyl Cellosolve, diethyl ether, etc.: cyclic ethers such as dioxane, tetrahydrofuran, etc.; ketones such as acetone, etc.; esters such as ethyl acetate, etc.; dimethylformamide, dimethylacetamide, dimethylsulfoxide, water, and the like. These inert solvents may be used singly or as a mixture thereof.

As the base which can be used in this reaction, an organic base or an inorganic base can be used. Examples of the inorganic base include hydroxides or carbonates of alkali metal atoms such as sodium, potassium, etc. and alkaline earth metal atoms such as calcium, magnesium, etc.; hydrides of alkali metal atoms such as sodium hydride, etc. Examples of the organic base include alcoholates of alkali metal atoms such as sodium methoxide, potassium t-butoxide, etc.; aminated alkali metal atoms such as sodium amine, etc.; tertiary amines such as triethylamine, etc.; pyridine, 4-N,N-dimethylaminopyridine and the like.

As to the amount of the base used, the base may be used in the range chosen from an equimolar amount or an excess amount, based on the compound represented by the general formula (IV).

The reaction proceeds in an equimolar relation and it is thus sufficient to use the respective reactants in equimolar amounts. However, the halide represented by the general formula (V) may be used in an excess amount.

The reaction temperature is properly chosen in the range from room temperature to the boiling point of the inert solvent used.

Although the reaction time is varied depending on the degree of reaction, the reaction temperature and the like, it may be chosen in the range of several minutes to 48 hours.

After completion of the reaction, the reaction mixture is treated as in the reaction described above to prepare the desired product.

3. Process for preparing the compounds of general formula (IB) from the compounds of general formula (IA)

This reduction can be carried out in the presence of an appropriate reducing agent or by hydrogenation in the presence of a catalyst.

In the reaction using the reducing agent, reducing agents, e.g., $NaBH_3CN$, $NaBH_4$ and the like may be used. The amount of the reducing agent used is chosen in the range of an equimolar amount to an excess molar amount, when converted into the mol number of the hydride as the reducing agent, based on the hydrazone represented by the general formula (IA).

As the inert solvent which can be used in this reaction, any solvent may be used so long as it does not markedly inhibit the progress of the reaction. There can be exemplified alcohols such as methanol, ethanol, propanol, butanol, etc., linear ethers such as diethyl ether, etc.; cyclic ethers such as dioxane, tetrahydrofuran, etc.; cellosolves such as Methyl Cellosolve, etc.; esters such as ethylacetate, etc.; aromatic hydrocarbons such as benzene, toluene, xylene, etc.; halogenated hydrocarbons such as dichloromethane, chloroform, carbon tetrachloride, etc.; diglyme, dimethylformamide, dimethylacetamide, dimethylsulfoxide, sulfonate, water, and the like. These inert solvents may be used singly or as a mixture thereof.

This reaction is carried out under acidic to neutral conditions in the pH range of 1 to 7, preferably in the pH range of 4 to 6. The conditions may be adjusted by adding hydrogen chloride, hydrogen bromide, etc. to the reaction mixture.

The reaction temperature is properly chosen in the range of $-20°$ C. to the boiling point of the inert solvent used.

Although the reaction time is varied depending on the degree of reaction, the reaction temperature and the like, it may be chosen in the range of several minutes to 48 hours.

After completion of the reaction, the desired compound is isolated from a reaction solution in a conventional manner such as removal of the solvent by distillation, solvent extraction, etc., and if necessary and desired, purified by recrystallization, column chromatography, etc., whereby the desired compound can be prepared.

When catalytic hydrogenation is carried out as the reduction reaction, the reduction may be performed according to, for example, the conventional manner described in "SHIN-JIKKEN KAGAKU KOZA (Lecture Series on Experimental Chemistry)" (volume 15-II, Maruzen Publishing Co.). Examples of the inert solvent which can be used include alcohols such as methanol, ethanol, propanol, butanol, etc.; cellosolves such as Methyl Cellosolve, etc.; cyclic ethers such as dioxane, tetrahydrofuran, etc.; hydrocarbons such as hexane, cyclohexane, etc.; fatty acids or esters thereof such as acetic acid, ethyl acetate, N,N-dimethylformamide and the like. These inert solvents may be used singly or as a mixture thereof.

As the catalyst used in this reaction, there are, for example, palladium carbon, palladium black, platinum dioxide, Raney nickel, etc. which are representative catalysts used for catalytic hydrogenation. The amount of the catalyst used may be properly chosen in the range of 0.0001% by weight to 20% by weight based on the compound represented by the general formula (IA).

The hydrogen pressure in this reaction may be chosen in the range of normal pressure to 300 atmospheres, preferably in the range of normal pressure to 50 atmospheres.

The reaction temperature is properly chosen in the range from room temperature to the boiling point of the inert solvent used. The reaction is carried out preferably in the range of room temperature to 80° C.

Although the reaction time is varied depending on the degree of reaction, the reaction temperature and the like, it may be chosen in the range of several minutes to 80 hours.

After completion of the reaction, the reaction mixture is treated as in the case where the reducing agent is used, whereby the desired product can be prepared.

The compounds represented by the general formula (III) which are the starting compounds used to prepare the hydrazone derivatives of the present invention represented by the general formula (I) can be prepared by the methods described in Japanese Patent Application KOKAI (Laid-Open) Nos. 62-223169 and 64-70462, J. Org. Chem., 417 (1941), Bet., 56B, 1060–1065 (1923), etc.

The compounds represented by the general formula (IV) can be prepared by the process described in Collection Czech. Chem. Communs., 25, 2651–2667 (1960).

Typical examples of the hydrazone derivatives of the present invention represented by the general formula (IA) or (IB) are listed in Table 1 and Table 2 but the present invention is not deemed to be limited thereto.

TABLE 1

General Formula (IA)

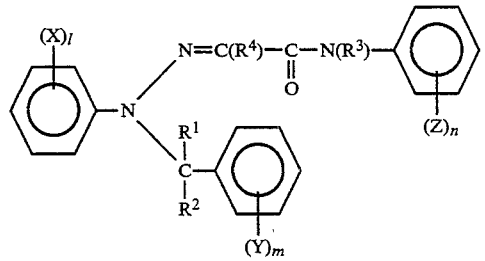

| No. | $R^1$ | $R^2$ | $R^3$ | $R^4$ | $(X)_l$ | $(Y)_m$ | $(Z)_n$ | Physical properties |
|---|---|---|---|---|---|---|---|---|
| 1A | H | H | H | H | H | H | H | m.p. 172.1° C. |
| 2A | H | H | H | H | H | H | 4-$CH_3$ | m.p. 155.2–152.9° C. |
| 3A | H | H | H | H | H | H | 4-$OCF_3$ | m.p. 113.3–114.0° C. |
| 4A | H | H | H | H | H | 4-Cl | 4-$CF_3$ | m.p. 159.7° C. |
| 5A | H | H | H | H | H | 4-Cl | 4-$OCF_3$ | m.p. 137.8° C. |
| 6A | H | H | H | H | H | 4-Cl | 4-$COCH_3$ | m.p. 187.9° C. |
| 7A | H | H | H | H | H | 4-CN | 4-Cl | m.p. 163° C. |
| 8A | H | H | H | H | H | 4-CN | 4-$CF_3$ | m.p. 184–185° C. |
| 9A | H | H | H | H | H | 4-CN | 4-$OCF_3$ | m.p. 138° C. |
| 10A | H | H | H | H | H | 4-$CO_2CH_3$ | 4-$OCF_3$ | m.p. 159° C. |
| 11A | H | H | H | H | H | 4-$CO_2C_4H_4$-t | 4-$OCH_3$ | m.p. 142.2–143.7° C. |
| 12A | H | H | H | H | 3-Cl | 4-Cl | 2-Cl | m.p. 135.5–137.0° C. |
| 13A | H | H | H | H | 3-Cl | 4-Cl | 3-Cl | m.p. 136.3° C. |
| 14A | H | H | H | H | 3-Cl | 4-Cl | 4-Cl | m.p. 143.5–144.0° C. |
| 15A | H | H | H | H | 3-Cl | 4-Cl | 3-$CH_3$ | m.p. 128.5° C. |
| 16A | H | H | H | H | 3-Cl | 4-Cl | 4-$CH_3$ | m.p. 149.6–150.0° C. |
| 17A | H | H | H | H | 3-Cl | 4-Cl | 4-$OCF_3$ | m.p. 139.6–141.5° C. |
| 18A | H | H | H | H | 3-Cl | 4-$NO_2$ | 4-Cl | m.p. 174.0–176.5° C. |
| 19A | H | H | H | H | 3-Cl | 4-$NO_2$ | 4-$OCF_3$ | m.p. 151.6–151.7° C. |
| 20A | H | H | H | H | 3-Cl | 4-CN | 4-Cl | m.p. 191.0–192.0° C. |
| 21A | H | H | H | H | 3-Cl | 4-CN | 4-$CF_3$ | m.p. 202.9° C. |
| 22A | H | H | H | H | 3-Cl | 4-CN | 4-$OCF_3$ | m.p. 160.5–162.0° C. |
| 23A | H | H | H | H | 3-Cl | 4-CN | 4-$SCF_3$ | m.p. 188.0° C. |
| 24A | H | H | H | H | 3-Cl | 4-CN | 4-$SOCF_3$ | m.p. 206.1° C. |
| 25A | H | H | H | H | 3-Cl | 4-$OCF_3$ | 4-$CF_3$ | m.p. 144° C. |
| 26A | H | H | H | H | 3-Cl | 4-$OCF_3$ | 4-$OCF_3$ | m.p. 130–131° C. |
| 27A | H | H | H | H | 4-Cl | 4-$NO_2$ | 4-Cl | m.p. 162.2° C. |
| 28A | H | H | H | H | 4-Cl | 4-$NO_2$ | 4-$OCF_3$ | m.p. 111.0–115.1° C. |
| 29A | H | H | H | H | 3-F | 4-CN | 4-Cl | m.p. 154–156° C. |
| 30A | H | H | H | H | 3-F | 4-CN | 4-$CF_3$ | m.p. 178° C. |
| 31A | H | H | H | H | 3-F | 4-CN | 4-$OCF_3$ | m.p. 155.9–156.8° C. |
| 32A | H | H | H | H | 3-$CH_3$ | 4-CN | 4-Cl | m.p. 127° C. |
| 33A | H | H | H | H | 3-$CH_3$ | 4-CN | 4-$CF_3$ | m.p. 153–155° C. |
| 34A | H | H | H | H | 3-$CH_3$ | 4-CN | 4-$OCF_3$ | m.p. 166° C. |
| 35A | H | H | H | H | 4-$CH_3$ | 4-Cl | 4-$CF_3$ | m.p. 167.9–169.5° C. |
| 36A | H | H | H | H | 4-$CH_3$ | 4-Cl | 4-$OCF_3$ | m.p. 167.4° C. |
| 37A | H | H | H | H | 4-$CH_3$ | 4-CN | 4-$OCF_3$ | m.p. 150.6–151.2° C. |
| 38A | H | H | H | H | 3-$CF_3$ | 4-CN | 4-Cl | m.p. 164–165° C. |
| 39A | H | H | H | H | 3-$CF_3$ | 4-CN | 4-F | m.p. 173–175° C. |
| 40A | H | H | H | H | 3-$CF_3$ | 4-CN | 4-Br | m.p. 164° C. |
| 41A | H | H | H | H | 3-$CF_3$ | 4-CN | 4-I | m.p. 80° C. |
| 42A | H | H | H | H | 3-$CF_3$ | 4-CN | 4-$CF_3$ | m.p. 191.5–192.0° C. |
| 43A | H | H | H | H | 3-$CF_3$ | 4-CN | 4-$NO_2$ | m.p. 236–238° C. |

TABLE 1-continued

General Formula (IA)

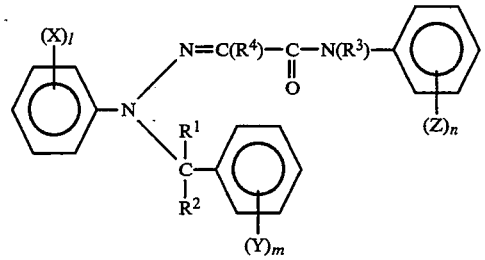

(IA)

| No. | $R^1$ | $R^2$ | $R^3$ | $R^4$ | $(X)_l$ | $(Y)_m$ | $(Z)_n$ | Physical properties |
|---|---|---|---|---|---|---|---|---|
| 44A | H | H | H | H | 3-$CF_3$ | 4-CN | 4-CN | m.p. 174.5–175.1° C. |
| 45A | H | H | H | H | 3-$CF_3$ | 4-CN | 3-$CF_3$ | m.p. 151.1–152.5° C. |
| 46A | H | H | H | H | 3-$CF_3$ | 4-CN | 4-$OCH_3$ | m.p. 167° C. |
| 47A | H | H | H | H | 3-$CF_3$ | 4-CN | 4-$OCF_3$ | m.p. 151.0° C. |
| 48A | H | H | H | H | 3-$CF_3$ | 4-CN | 4-O-C$_6$H$_5$ | m.p. 156° C. |
| 49A | H | H | H | H | 3-$CF_3$ | 4-CN | 2,4-$Cl_2$ | m.p. 78° C. |
| 50A | H | H | H | H | 3-$CF_3$ | 4-CN | 3,4-$Cl_2$ | m.p. 213° C. |
| 51A | H | H | H | H | 3-$CF_3$ | 4-CN | 3,5-$Cl_2$ | m.p. 169° C. |
| 52A | H | H | H | H | 3-$CF_3$ | 4-CN | 3-Cl-4-F | m.p. 194° C. |
| 53A | H | H | H | H | 3-$CF_3$ | 4-$CF_3$ | 4-$CF_3$ | m.p. 144.2° C. |
| 54A | H | H | H | H | 3-$CF_3$ | 4-$CF_3$ | 4-$OCF_3$ | m.p. 142.6–144.7° C. |
| 55A | H | H | H | H | 3-$CF_3$ | 4-$OCHF_2$ | 4-Cl | m.p. 124° C. |
| 56A | H | H | H | H | 3-$CF_3$ | 4-$OCHF_2$ | 4-$CF_3$ | m.p. 108° C. |
| 57A | H | H | H | H | 3-$CF_3$ | 4-$OCHF_2$ | 4-$OCF_3$ | m.p. 105–106° C. |
| 58A | H | H | H | H | 3-$CF_3$ | 4-$SCH_3$ | 4-Cl | m.p. 146° C. |
| 59A | H | H | H | H | 3-$CF_3$ | 4-$SCH_3$ | 4-$OCF_3$ | m.p. 134° C. |
| 60A | H | H | H | H | 3-$CF_3$ | 4-$SOCH_3$ | 4-$OCF_3$ | m.p. 171° C. |
| 61A | H | H | H | H | 3-$CF_3$ | 4-$SO_2CH_3$ | 4-$OCF_3$ | m.p. 193–194° C. |
| 62A | H | H | H | H | 3,4-$Cl_2$ | 4-CN | 4-$CF_3$ | m.p. 224–231° C. |
| 63A | H | H | H | H | 3,4-$Cl_2$ | 4-CN | 4-$OCF_3$ | m.p. 224.0° C. |
| 64A | H | H | H | H | 3,5-$Cl_2$ | 4-CN | 4-$CF_3$ | m.p. 255.5–258.0° C. |
| 65A | H | H | H | H | 3,5-$Cl_2$ | 4-CN | 4-$OCF_3$ | m.p. 221.7–223.3° C. |
| 66A | H | $CH_3$ | H | H | 4-Cl | 4-Cl | 4-Cl | paste |
| 67A | H | $CH_3$ | H | H | 4-Cl | 4-Cl | 4-$OCF_3$ | paste |
| 68A | H | H | H | $CH_3$ | 3-Cl | 4-CN | 4-$OCF_3$ | nD 1.5950 (25° C.) |
| 69A | H | H | H | $CH_3$ | 4-Cl | 4-Cl | H | nD 1.6355 (27° C.) |
| 70A | H | H | H | $CH_3$ | 4-Cl | 4-Cl | 4-Cl | paste |
| 71A | H | H | H | $CH_3$ | 4-Cl | 4-Cl | 4-$OCF_3$ | nD 1.5939 (27° C.) |
| 72A | H | H | $CH_3$ | H | 3-$CF_3$ | 4-CN | 4-Cl | m.p. 209–211° C. |
| 73A | H | H | $CH_3$ | H | 3-$CF_3$ | 4-CN | 4-$CF_3$ | m.p. 181° C. |
| 74A | H | H | H | H | 3-$CF_3$ | 4-$SO_2CH_3$ | 4-Cl | m.p. 228° C. |
| 75A | H | H | H | H | 3-$CF_3$ | 4-$SOCH_3$ | 4-Cl | m.p. 178° C. |
| 76A | H | H | H | H | 3-$CF_3$ | 4-CN | 4-$OSO_2CF_3$ | m.p. 172° C. |
| 77A | H | H | H | H | 3-$CF_3$ | 4-CN | 4-$OCF_2CHF_2$ | m.p. 153° C. |
| 78A | H | H | H | H | 3-$CF_3$ | 4-$SCHF_2$ | 4-$OCF_3$ | m.p. 134° C. |
| 79A | H | H | H | H | 3-$CF_3$ | 4-$SCHF_2$ | 4-Cl | m.p. 143° C. |
| 80A | H | H | H | H | 3-$CF_3$ | 4-$SCHF_2$ | 4-Br | m.p. 145° C. |
| 81A | H | H | H | H | 3-$CF_3$ | 4-$SOCHF_2$ | 4-$OCF_3$ | m.p. 143° C. |
| 82A | H | H | H | H | 3-$CF_3$ | 4-$SOCHF_2$ | 4-Cl | m.p. 181° C. |
| 83A | H | H | H | H | 3-$CF_3$ | 4-$SOCHF_2$ | 4-Br | m.p. 171° C. |
| 84A | H | H | H | H | 3-$CF_3$ | 4-$SO_2CHF_2$ | 4-$OCF_3$ | m.p. 109–110° C. |
| 85A | H | H | H | H | 3-$CF_3$ | 4-$SO_2CHF_2$ | 4-Cl | m.p. 222° C. |
| 86A | H | H | H | H | 3-$CF_3$ | 4-$SO_2CHF_2$ | 4-Br | m.p. 213° C. |
| 87A | H | H | H | H | 3-$NO_2$ | 4-CN | 4-$OCF_3$ | m.p. 190–191° C. |
| 88A | H | H | H | H | 3-$NO_2$ | 4-CN | 4-$CF_3$ | m.p. 213–215° C. |
| 89A | H | H | H | H | 3-$NO_2$ | 4-CN | 4-Cl | m.p. 205° C. |
| 90A | H | H | H | H | 3-$NO_2$ | 4-CN | 4-Br | m.p. 215–217° C. |
| 91A | H | H | H | H | 3-$C_2H_5$ | 4-CN | 4-$OCF_3$ | m.p. 157° C. |
| 92A | H | H | H | H | 3-$C_2H_5$ | 4-CN | 4-$CF_3$ | m.p. 166° C. |
| 93A | H | H | H | H | 3-$C_2H_5$ | 4-CN | 4-Cl | m.p. 142° C. |
| 94A | H | H | H | H | 3-$C_2H_5$ | 4-CN | 4-Br | m.p. 133° C. |
| 95A | H | H | H | H | 3-$OCH_3$ | 4-CN | 4-$OCF_3$ | m.p. 154° C. |
| 96A | H | H | H | H | 3-$OCH_3$ | 4-CN | 4-$CF_3$ | m.p. 157° C. |
| 97A | H | H | H | H | 3-$OCH_3$ | 4-CN | 4-Cl | m.p. 169° C. |
| 98A | H | H | H | H | 3-$OCH_3$ | 4-CN | 4-Br | m.p. 153° C. |
| 99A | H | H | H | H | 4-$CH_3$ | 4-CN | 4-$OCF_3$ | m.p. 170° C. |
| 100A | H | H | H | H | 4-$CH_3$ | 4-CN | 4-$CF_3$ | m.p. 160° C. |
| 101A | H | H | H | H | 4-$CH_3$ | 4-CN | 4-Cl | m.p. 159° C. |
| 102A | H | H | H | H | 4-$CH_3$ | 4-CN | 4-Br | m.p. 178° C. |
| 103A | H | H | H | H | 4-Cl | 4-CN | 4-$OCF_3$ | m.p. 158° C. |

TABLE 1-continued

General Formula (IA)

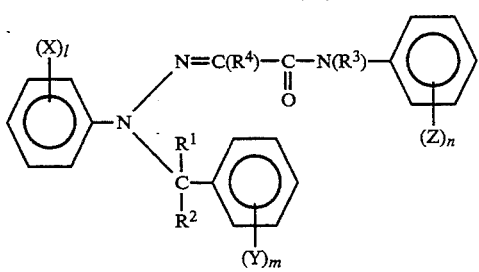

(IA)

| No. | $R^1$ | $R^2$ | $R^3$ | $R^4$ | $(X)_l$ | $(Y)_m$ | $(Z)_n$ | Physical properties |
|---|---|---|---|---|---|---|---|---|
| 104A | H | H | H | H | 4-Cl | 4-CN | 4-$CF_3$ | m.p. 168° C. |
| 105A | H | H | H | H | 4-Cl | 4-CN | 4-Cl | m.p. 211° C. |
| 106A | H | H | H | H | 2-Cl | 4-CN | 4-$OCF_3$ | nD 1.5892 (10° C.) |
| 107A | H | H | H | H | 3-Cl | 2-CN | 4-$OCF_3$ | m.p. 148° C. |
| 108A | H | H | H | H | 4-F-3-Cl | 4-CN | 4-$OCF_3$ | m.p. 187–189° C. |
| 109A | H | H | H | H | 4-F-3-Cl | 4-CN | 4-Cl | m.p. 184° C. |
| 110A | H | H | H | H | 3-$SCH_3$ | 4-CN | 4-$OCF_3$ | m.p. 126.6° C. |
| 111A | H | H | H | H | 3-$SCH_3$ | 4-CN | 4-Br | m.p. 162.6–163.1° C. |
| 112A | H | H | H | H | 3-$SOCH_3$ | 4-CN | 4-$OCF_3$ | m.p. 179.0–181.6° C. |
| 113A | H | H | H | H | 3-$SOCH_3$ | 4-CN | 4-Br | m.p. 129.8–130.6° C. |
| 114A | H | H | H | H | 3-$SO_2CH_2$ | 4-CN | 4-$OCF_3$ | m.p. 212–214° C. |
| 115A | H | H | H | H | 3-$SO_2CH_3$ | 4-CN | 4-Br | m.p. 199.5–200.1° C. |
| 116A | H | H | H | H | 3-Cl | 4-C≡CH | 4-$OCF_3$ | m.p. 173.8° C. |

TABLE 2

General Formula (IB)

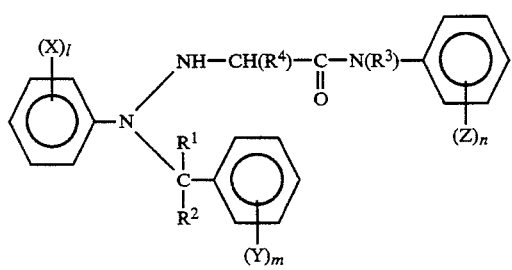

(IB)

| No. | $R^1$ | $R^2$ | $R^3$ | $R^4$ | $(X)_l$ | $(Y)_m$ | $(Z)_n$ | Physical properties |
|---|---|---|---|---|---|---|---|---|
| 1B | H | H | H | H | H | H | H | m.p. 119.0–122.0° C. |
| 2B | H | H | H | H | H | H | 4-$CH_3$ | m.p. 88.0–91.0° C. |
| 3B | H | H | H | H | H | H | 4-$OCF_3$ | m.p. 51.0–53.0° C. |
| 4B | H | H | H | H | H | 4-Cl | 4-$OCF_3$ | m.p. 92.1° C. |
| 5B | H | H | H | H | H | 4-CN | 4-Cl | m.p. 106–108° C. |
| 6B | H | H | H | H | H | 4-CN | 4-$CF_3$ | m.p. 70–72° C. |
| 7B | H | H | H | H | H | 4-CN | 4-$OCF_3$ | nD 1.5685 (27° C.) |
| 8B | H | H | H | H | 3-Cl | 4-Cl | 4-Cl | m.p. 105.3–106.4° C. |
| 9B | H | H | H | H | 3-Cl | 4-Cl | 3-$CH_3$ | nD 1.5572 (26° C.) |
| 10B | H | H | H | H | 3-Cl | 4-Cl | 4-$CH_3$ | m.p. 91.2–92.6° C. |
| 11B | H | H | H | H | 3-Cl | 4-Cl | 4-$OCF_3$ | m.p. 38.0° C. |
| 12B | H | H | H | H | 3-Cl | 4-$NO_2$ | 4-Cl | paste |
| 13B | H | H | H | H | 3-Cl | 4-$NO_2$ | 4-$OCF_3$ | paste |
| 14B | H | H | H | H | 3-Cl | 4-CN | 4-Cl | m.p. 153.1° C. |
| 15B | H | H | H | H | 3-Cl | 4-CN | 4-$CF_3$ | m.p. 141.1–141.8° C. |
| 16B | H | H | H | H | 3-Cl | 4-CN | 4-$OCF_3$ | m.p. 43.5–45.0° C. |
| 17B | H | H | H | H | 3-Cl | 4-$OCF_3$ | 4-$OCF_3$ | nD 1.5371 (26° C.) |
| 18B | H | H | H | H | 3-Cl | 4-$OCF_3$ | 4-$CF_3$ | m.p. 62.3° C. |
| 19B | H | H | H | H | 4-Cl | 4-$NO_2$ | 4-$OCF_3$ | nD 1.5823 (17° C.) |
| 20B | H | H | H | H | 3-F | 4-CN | 4-Cl | m.p. 164–165° C. |
| 21B | H | H | H | H | 3-F | 4-CN | 4-$CF_3$ | m.p. 46° C. |
| 22B | H | H | H | H | 3-F | 4-CN | 4-$OCF_3$ | nD 1.5615 (27° C.) |
| 23B | H | H | H | H | 3,5-$Cl_2$ | 4-CN | 4-$OCF_3$ | nD 1.5611 (21° C.) |
| 24B | H | H | H | H | 3-$CH_3$ | 4-CN | 4-Cl | m.p. 138–139° C. |
| 25B | H | H | H | H | 3-$CH_3$ | 4-CN | 4-$CF_3$ | nD 1.5475 (28° C.) |
| 26B | H | H | H | H | 3-$CH_3$ | 4-CN | 4-$OCF_3$ | nD 1.5315 (28° C.) |
| 27B | H | H | H | H | 4-$CH_3$ | 4-Cl | 4-$OCF_3$ | m.p. 79.5–82.0° C. |
| 28B | H | H | H | H | 3-$CF_3$ | 4-CN | 4-Cl | m.p. 43° C. |
| 29B | H | H | H | H | 3-$CF_3$ | 4-CN | 4-F | m.p. 133–135° C. |
| 30B | H | H | H | H | 3-$CF_3$ | 4-CN | 4-Br | m.p. 68° C. |
| 31B | H | H | H | H | 3-$CF_3$ | 4-CN | 4-I | paste |
| 32B | H | H | H | H | 3-$CF_3$ | 4-CN | 4-$CF_3$ | nD 1.5521 (21° C.) |
| 33B | H | H | H | H | 3-$CF_3$ | 4-CN | 4-$OCF_3$ | m.p. 153.1° C. |

TABLE 2-continued

General Formula (IB)

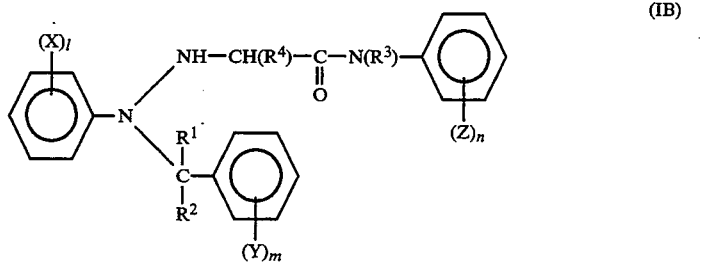

| No. | R$^1$ | R$^2$ | R$^3$ | R$^4$ | (X)$_l$ | (Y)$_m$ | (Z)$_n$ | Physical properties |
|---|---|---|---|---|---|---|---|---|
| 34B | H | H | H | H | 3-CF$_3$ | 4-CF$_3$ | 4-CF$_3$ | m.p. 114–116° C. |
| 35B | H | H | H | H | 3-CF$_3$ | 4-CF$_3$ | 4-OCF$_2$ | m.p. 62.0–63.0° C. |
| 36B | H | H | H | H | 3-CF$_3$ | 4-OCHF$_2$ | 4-Cl | nD 1.5440 (24° C.) |
| 37B | H | H | H | H | 3-CF$_3$ | 4-OCHF$_2$ | 4-CF$_3$ | m.p. 80–81° C. |
| 38B | H | H | H | H | 3-CF$_3$ | 4-OCHF$_2$ | 4-OCF$_3$ | m.p. 71–72° C. |
| 39B | H | H | H | H | 3-CF$_3$ | 4-SCH$_3$ | 4-Cl | m.p. 158° C. |
| 40B | H | H | H | H | 3-CF$_3$ | 4-SCH$_3$ | 4-OCF$_3$ | m.p. 112° C. |
| 41B | H | H | H | H | 3-CF$_3$ | 4-SOCH$_3$ | 4-OCF$_3$ | m.p. 63° C. |
| 42B | H | H | H | H | 3-CF$_3$ | 4-SO$_2$CH$_3$ | 4-OCF$_3$ | m.p. 116° C. |
| 43B | H | H | H | H | 3-CF$_3$ | 4-CN | 4-OSO$_2$CF$_3$ | nD 1.5235 (18° C.) |
| 44B | H | H | H | H | 3-CF$_3$ | 4-SO$_2$CH$_3$ | 4-OCF$_2$CHF$_2$ | m.p. 108° C. |
| 45B | H | H | H | H | 3-CF$_3$ | 4-SOCH$_3$ | 4-Cl | nD 1.5835 (18° C.) |
| 46B | H | H | H | H | 3-CF$_3$ | 4-SCHF$_2$ | 4-OCF$_3$ | m.p. 102° C. |
| 47B | H | H | H | H | 3-CF$_3$ | 4-SCHF$_2$ | 4-Cl | nD 1.5580 (12° C.) |
| 48B | H | H | H | H | 3-CF$_3$ | 4-SCHF$_2$ | 4-Br | m.p. 82–84° C. |
| 49B | H | H | H | H | 3-CF$_3$ | 4-SOCHF$_2$ | 4-OCF$_3$ | m.p. 48° C. |
| 50B | H | H | H | H | 3-CF$_3$ | 4-SOCHF$_2$ | 4-Cl | nD 1.5840 (15° C.) |
| 51B | H | H | H | H | 3-CF$_3$ | 4-SO$_2$CHF$_2$ | 4-OCF$_3$ | nD 1.5470 (17° C.) |
| 52B | H | H | H | H | 3-NO$_2$ | 4-CN | 4-OCF$_3$ | m.p. 49° C. |
| 53B | H | H | H | H | 3-C$_2$H$_5$ | 4-CN | 4-OCF$_3$ | m.p. 127° C. |
| 54B | H | H | H | H | 3-C$_2$H$_5$ | 4-CN | 4-CF$_3$ | m.p. 83–86° C. |
| 55B | H | H | H | H | 3-C$_2$H$_5$ | 4-CN | 4-Cl | m.p. 94–97° C. |
| 56B | H | H | H | H | 3-C$_2$H$_5$ | 4-CN | 4-Br | m.p. 107–109° C. |
| 57B | H | H | H | H | 3-OCH$_3$ | 4-CN | 4-OCF$_3$ | m.p. 82° C. |
| 58B | H | H | H | H | 4-CH$_3$ | 4-CN | 4-OCF$_3$ | nD 1.5630 (20° C.) |
| 59B | H | H | H | H | 4-CH$_3$ | 4-CN | 4-Cl | m.p. 115° C. |
| 60B | H | H | H | H | 4-CH$_3$ | 4-CN | 4-Br | m.p. 109° C. |
| 61B | H | H | H | H | 3-SCH$_3$ | 4-CN | 4-OCF$_3$ | m.p. 124.1–126.9° C. |
| 62B | H | H | H | H | 3-SOCH$_3$ | 4-CN | 4-OCF$_3$ | m.p. 133.6–134.1° C. |
| 63B | H | H | H | H | 3-SO$_2$CH$_3$ | 4-CN | 4-OCF$_3$ | m.p. 71.1° C. |
| 64B | H | H | H | H | 3-Cl | 4-C≡CH | 4-OCH$_3$ | m.p. 128.6° C. |

Table 3 shows NMR data of the compounds having physical properties as paste listed in Tables 1 and 2.

TABLE 3

| No. | NMR [CDCl$_3$/TMS, δ value(ppm)] |
|---|---|
| 70A | 1.82(3H, s), 4.72(2H, s), 6.73–7.80(12H, m), 8.95(1H, s). |
| 12B | 3.65(2H, d), 4.20(1H, t), 4.70(2H, s), 6.85(1H, d.d), 6.93(1H, d.d), 7.08(1H, d.d), 7.15–7.21(3H, m), 7.24(2H, d), 7.40(2H, d), 8.13(2H, d), 8.40(1H, s). |
| 13B | 3.64(2H, s), 4.69(2H, s), 6.84(1H, d.d), 6.94(1H, d.d), 7.09(3H, m), 7.23(1H, t), 7.29(2H, d), 7.40(2H, d), 8.12(2H, d), 8.40(1H, s). |
| 31B | 3.62(2H, s), 4.69(2H, s), 7.00–7.60(12H, m), 8.35(1H, s). |

Typical examples of the present invention are described below but should not be construed as limiting the scope of the invention.

EXAMPLE 1

1-1 Production of 2-[N-(4-cyanobenzyl)-N-(3-trifluoromethylphenyl)]hydrazonacetic acid

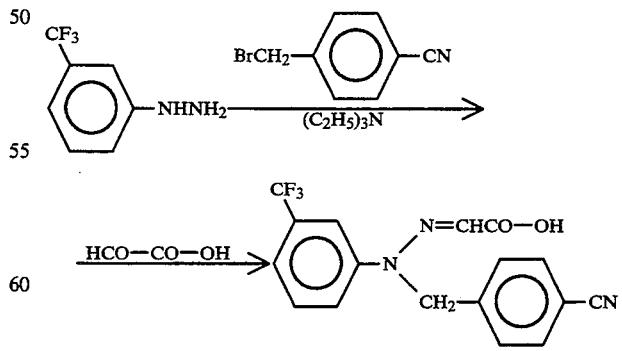

In 100 ml of toluene was dissolved 13.46 g (76.5 mmole) of 3-trifluoromethylphenylhydrazine followed by adding 8.12 g (80.4 mmole) of triethylamine and 1.499 g (76.5 mmole) of 4-cyanobenzyl bromide thereto. The mixture was stirred at reflux at 3 hours.

After completion of the reaction, the reaction solution was washed with water (50 mm×2) and the organic phase was concentrated. The concentrate was then dissolved in 80 ml of ethanol and under ice cooling, 11.51 g (62.2 mmole) of 40% glyoxylic acid aqueous solution was dropwise added to the solution. The solution was stirred for 2 hours at room temperature.

After completion of the reaction, the solvent was distilled off from the reaction solution containing the product and 50 ml of water was added to the residue followed by extraction with ethyl acetate (100 mm×2). The extract was dried over anhydrous sodium sulfate and concentrated under reduced pressure. The precipitated crystals were washed with hexane-ether solvent mixture to give 13.02 g of the desired product.

Physical properties: m.p. 220° C. Yield: 60.2%

1-2 Production of 2-[N-(4-cyanobenzyl)-N-(3-trifluoromethylphenyl)]hydrazono-4-chloroacetanilide (Compound No. 38A)

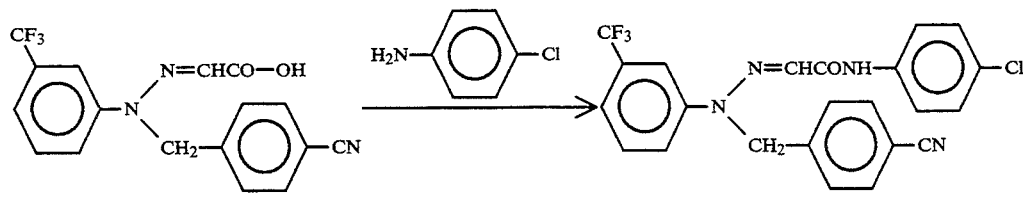

In 7 ml of carbon tetrachloride was suspended 0.59 g (1.7 mmole) of 2-[N-(4-cyanobenzyl)-N-(3-trifluoromethylphenyl)]hydrazonoacetic acid obtained in 1-1 followed by adding 0.40 g (3.4 mmole) of thionyl chloride. The stirring mixture was heated at reflux for 1.5 hours.

After completion of the reaction, the reaction solvent was distilled off under reduced pressure. The resulting acid chloride was added to a solution of 0.62 g (1.7 mmole) of 4-chloroaniline and 0.37 g (3.7 mmole) of triethylamine in tetrahydrofuran. The mixture was stirred for an hour at room temperature.

After completion of the reaction, 10 ml of water was added to the reaction solution and the product was extracted with ethyl acetate (100 ml×2). The extract was dried over anhydrous sodium sulfate and concentrated under reduced pressure.

The resulting residue was purified by silica gel column chromatography (hexane-ethyl acetate) to give 0.51 g of the desired product.

Physical properties: m.p. 164°–165° C. Yield: 65.0%

EXAMPLE 2

Production of 2-[N-(3-chlorophenyl)-N-(4-cyanobenzyl)]hydrazono-4-trifluoromethoxyacetanilide (Compound No. 22A)

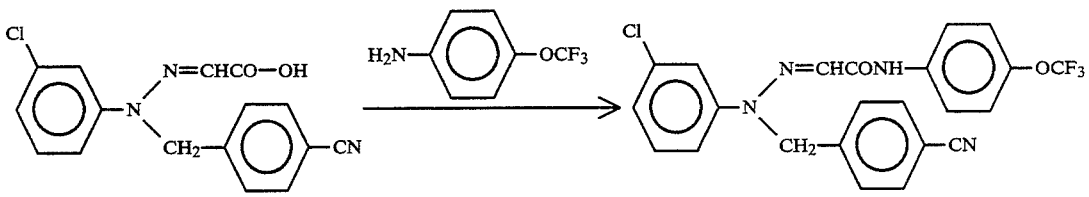

In 20 ml of pyridine were dissolved 1.50 g (4.8 mmole) of 2-[N-(3-chlorophenyl)-N-(4-cyanobenzyl)-]hydrazonoacetic acid prepared in a manner similar to in 1-1, 1.34 g (5.3 mmole) of 2-chloro-1-methylpyridinium iodide and 0.85 g (4.8 mmoles) of 4-trifluoromethoxyaniline. The stirring solution was heated at reflux for 3 hours.

After completion of the reaction, the solvent was distilled off and 30 ml of water was added to the residue. The product was extracted with ethyl acetate (50 ml×2). The extract was dried over anhydrous sodium sulfate and concentrated under reduced pressure.

The resulting residue was purified by silica gel column chromatography (hexane-ethyl acetate) to give 1.64 g of the desired product.

Physical properties: m.p. 160.5°–162.0° C. Yield: 72.3%

EXAMPLE 3

Production of 2-[N-(4-chlorophenyl)-N-(4-nitrobenzyl)]hydrazono-4-trifluoromethoxyacetanilide (Compound No. 28A)

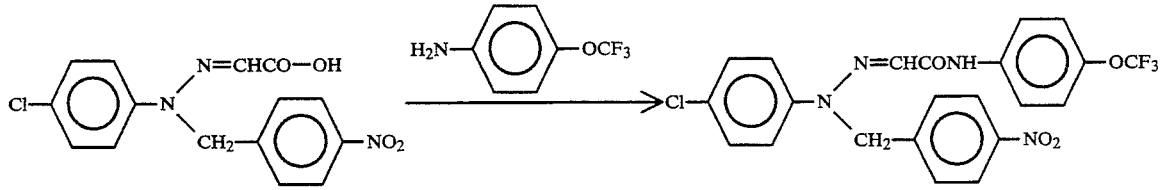

In 10 ml of tetrahydrofuran were dissolved 1.30 g (3.9 mmole) of 2-[N-(4-chlorophenyl)-N-(4-nitrobenzyl)]hydrazonoacetic acid prepared in a manner similar to in 1-1 and 0.63 g (3.9 mmole) of carbonyldiimidazole. The solution was stirred at room temperature for 5 hours.

After completion of the reaction, 30 ml of water was added to the reaction mixture followed by extracting with ethyl acetate (50 ml×2). The extract was dried over anhydrous sodium sulfate and concentrated under reduced pressure. The resulting residue was dissolved in 20 ml of pyridine and 0.69 g (3.9 mmole) of 4-trifluoromethoxyaniline and 0.10 g (0.8 mmole) of 4-N,N-dimethylaminopyridine were added to the solution. The stirring mixture was heated at reflux for 12 hours with stirring.

After completion of the reaction, the solvent was distilled off and 30 ml of water was added to the residue. The product was extracted with ethyl acetate (50 ml×2). The extract was dried over anhydrous sodium sulfate and concentrated under reduced pressure. The resulting residue was purified by silica gel column chromatography (hexane-ethyl acetate) to give 0.95 g of the desired product.

Physical properties: m.p. 111.0°–115.1° C. Yield: 49.5%.

EXAMPLE 4

4-1 Production of
2-phenylhydrazono-4-trifluoromethoxyacetanilide

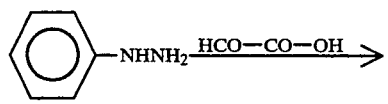

ture to give 20.2 g of phenylhydrazonoacetic acid (yield: 43.9%).

A solution of 7.81 g (47.6 mmole) of phenylhydrazonoacetic acid thus obtained and 10.58 g (104.7 mmole) of triethylamine in 30 ml of dichloromethane was dropwise added to a solution of 12.17 g (47.6 mmole) of 2-chloro-1-methylpyridinium iodide and 8.43 g (47.6 mmole) of 4-trifluoromethoxyaniline in 100 ml of dichloromethane. The mixture was stirred at room temperature for 5 hours.

After completion of the reaction, the solvent was distilled off and 50 ml of water was added to the residue. The product was extracted with ethyl acetate (100 ml×2). The extract was dried over anhydrous sodium sulfate and concentrated under reduced pressure. The resulting residue was purified by silica gel column chromatography (hexane-ethyl acetate) to give 7.62 g of the desired product.

Physical properties: m.p. 151.2°–154.3° C. Yield: 49.6%.

4-2 Production of
tert-butyl-4-[2-(4-trifluoromethoxyphenylcarbamoylmethylene)-1-phenylhydrazonomethyl]-benzoic acid
(Compound No. 11A)

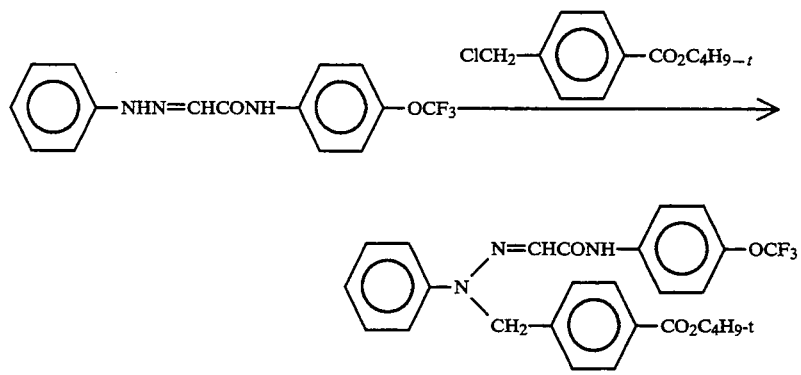

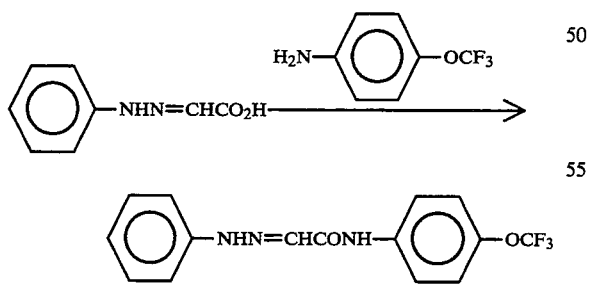

In 200 ml of ethanol was dissolved 30.24 g (0.28 mmole) of phenylhydrazine. Under ice cooling, 51.80 g (0.28 mmole) of 40% glyoxylic acid aqueous solution was dropwise added to the solution. The mixture was stirred at room temperature for 2 hours.

After completion of the reaction, the solvent was distilled off under reduced pressure. The precipitated crystals were washed with hexane-ether solvent mix- In 20 ml of dimethylformamide was dissolved 71 g (2.2 mmole) of phenylhydrazono-4-trifluoromethoxyacetanilide obtained in 4-1. Under ice cooling, 27 g (2.4 mmole) of potassium tert-butoxide and 0.54 g of tert-butyl 4-chloromethylbenzoate were added to the solution. The mixture was stirred at room temperature for 3 hours.

After completion of the reaction, 50 ml of ice water was added to the reaction mixture and the product was extracted with ethyl acetate (100 ml×2 ). The extract was dried over anhydrous sodium sulfate and concentrated under reduced pressure. The resulting residue was purified by silica gel column chromatography (hexane-ethyl acetate) to give 0.70 g of the desired product.

Physical properties: m.p. 142.2°–143.7° C. Yield: 70.0%.

EXAMPLE 5

Production of 2-[N-(4-cyanobenzyl)-N-(3-trifluoromethylphenyl)]hydrazino-4-chloroacetanilide (Compound No. 28B)

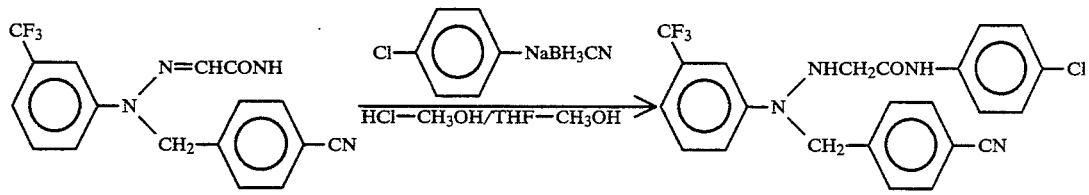

In a solvent mixture of 2 ml of tetrahydrofuran and 5 ml of methanol was dissolved 0.20 g (0.4 mmole) of 2-[N-(4-cyanobenzyl)-N-(3-trifluoromethylphenyl)]hydrazono -4-chloroacetanilide followed by adding 0.10 g (1.6 mmole) of sodium cyanoborohydride. With stirring, 0.7 ml of saturated hydrogen chloride-methanol solution was added to the mixture at room temperature. Stirring was continued for an hour at room temperature.

After completion of the reaction, the solvent was distilled off and ethyl acetate was added to the residue. The mixture was neutralized with sodium bicarbonate aqueous solution. The ethyl acetate phase was fractionated, dried over anhydrous sodium sulfate and concentrated under reduced pressure.

The resulting residue was purified by silica gel column chromatography (hexane-ethyl acetate) to give 0.18 g of the desired product.

Physical properties: m.p. 43° C. Yield: 89.2%.

EXAMPLE 6

Production of 2-[N-(4-cyanobenzyl)-N-(3-trifluoromethylphenyl)]hydrazino-4-fluoromethoxyacetanilide (Compound No. 33B)

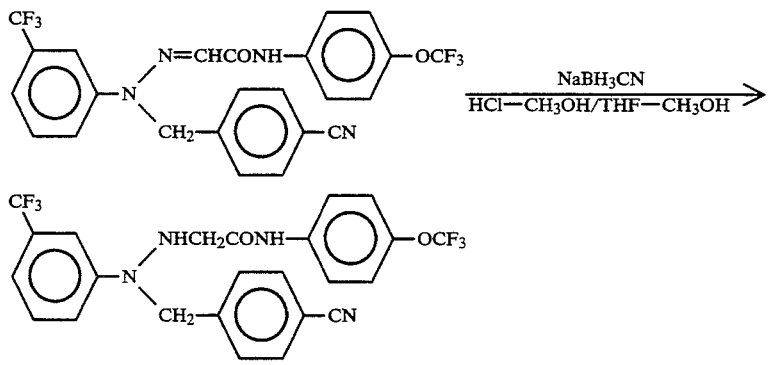

In a solvent mixture of 3 ml of tetrahydrofuran and 7 ml of methanol was dissolved 0.40 g (0.8 mmole) of 2-[N-(4-cyanobenzyl)-N-(3-trifluoromethylphenyl)]hydrazono-4-trifluoromethoxyacetanilide followed by adding 0.05 g (0.8 mmole) of sodium cyanoborohydride. With stirring, 0.5 ml of saturated hydrogen chloride-methanol solution was added to the mixture at room temperature. Stirring was continued for an hour at room temperature.

After completion of the reaction, the solvent was distilled off and ethyl acetate was added to the residue. The mixture was neutralized with sodium bicarbonate aqueous solution. The ethyl acetate phase was fractionated, dried over anhydrous sodium sulfate and concentrated under reduced pressure.

The resulting residue was purified by silica gel column chromatography (hexane-ethyl acetate) to give 0.38 g of the desired product.

The desired compound showed physical properties as paste (nD 1.5410, 21° C.) but can be isolated as crystals when it was allowed to stand.

Physical properties: m.p. 153.1° C. Yield: 93.5%.

Insecticides containing the hydrazone derivative of the general formula (I) of the present invention as an active ingredient are suitable for controlling various insect pests such as agricultural insect pests, forest insect pests, horticultural insect pests, stored grain insect pests, sanitary insect pests, nematodes, etc. They have an insecticidal effect also, for example, on LEPIDOPTERA including summer fruit tortrix (*Adoxophyes orana* fasciata), smaller tea tortrix (*Adoxophes sp.*), Manchurian fruit moth (*Grapholita inopinata*), oriental fruit moth (*Grapholita mlesta*), soybean pod border (*Leguminivora glycinivorella*), mulberry leafroller (*Olethreutes mori*), tea leafroller (*Caloptilla thevivora*), *Caloptilia sp.* (*Caloptilia zachrysa*), apple leafminer (*Phyllonorycter rengoniella*), pear barkminer (*Spulerina astaurota*), common white (*Piers rapae crucivora*), tabacco budworm (*Heliothis armigera*), codling moth (*Laspeyresia pomonella*), diamondback moth (*Plutella xylostella*), apple fruit moth (*Argyresthia conjugella*), peach fruit moth (*Carposina niponensis*), rice stem borer (*Chilo suppressalia*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape white fly (*Aleurolobus taonabae*), sweetpotato whitefly (*Bemisia tabaci*), greenhouse white fly (*Trialeurodes vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis yanonensis*), etc.; COLEOPTERA including soybean beetle (*Anomala rufocuprea*), Japanese beetle (*Popillia japonica*), tabacco beetle (*Lasioderma serricorne*), powderpost beetle (*Lyctus brunneus*), twenty-eight-spotted ladybird (*Epilachna vigintioctopunctata*), adzuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorphoptrus oryzophilus*), cucurbit leaf beetle (*Aulacophora femoralis*), rice leaf beetle (*Outlema oryzae*), striped flea beetle (*Phyllotreta striolata*), pine shoot beetle (*Tomicus piniperda*), Colorado potato beetle (*Leptinotarsa decemilineata*), Mexican bean beetle (*Epilachna varivestis*), corn rootworm (*Diabrotica sp.*), etc.; DIPTERA including melon fly (*Dacus(Zeugodacus) cucurbitae*), oriental fruit fly (*Dacus(Bactrocera) dorsalis*), rice leafminer (*Agromyza oryzae*), onion maggot (*Delia antiqua*), seedcorn maggot (*Delia platura*), soybean pod gall midge (*Asphodylia sp.*), muscid fly (*Musca domestica*), house mosquite (*Culex pipiens*), etc.; and TYLENCHIDA including root-lesion nematode (*Pratylenchus sp.*), coffer root-lesion nematode (*Pratylenchus coffeae*), potato cyst nematode (*Globodera rostochiensis*), root-knot nematode (*meloidogyne sp.*), citrus nematode (*Tylenchulus semipenetrans*), *Aphelenchus sp.* (*Aphelenchus avenae*), chrysanthemum foliar nematode (*Aphelenchoides ritzemabosi*), etc. The insecticides are markedly effective particularly against insect pests belonging to LEPIDOPTERA, COLEOPTERA and the like.

The zoological names and the like are in accordance with Applied Zoology and Entomology Society of Japan, "List of Agricultural and Forest Injurious Animals and Insects", published in 1987.

The agricultural and horticultural insecticide of the present invention has a marked insecticidal effect on the above-exemplified insect pests, sanitary insect pests, and/or nematodes, which are injurious to paddy fields, fruit trees, vegetables and other crops, and flowers and ornament plants. Therefore, the desired effect of the insecticide of the present invention can be obtained by applying the insecticide to the paddy field water, stalks and leaves of fruit trees, vegetables, other crops, flowers and ornament plants soil, etc., or to the inside of a house or ditches around a house, in which the above-exemplified sanitary insect pests injurious to men and beasts appear or are expected to appear. The application is carried out at a season at which the insect pests, sanitary insect pests or nematodes are expected to appear, before their appearance or at the time when their appearance is confirmed.

This invention however should not be limited to these embodiments.

When the hydrazone derivative of the general formula (I) of this invention is used as an insecticide, it is generally prepared into conveniently usable forms according to an ordinary manner for preparation of agrochemicals.

That is, the hydrazone derivative of the general formula (I) of this invention and, optionally, an adjuvant are blended with a suitable inert carrier in a proper proportion and prepared into a suitable preparation form such as a suspension, emulsifiable concentrate, soluble concentrate, wettable powder, granules, dust or tablet through dissolution, dispersion, suspension, mixing, impregnation, adsorption or sticking.

The inert carrier in this invention may be solid or liquid. Examples of the solid carrier are soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes [e.g. diatomaceous earth, silica sand, mica and white carbon, i.e. synthestic, high-dispersion silicic acid, also called finely divided hydrated silica or hydrated silicic acid, some of commercially available products contain silicate as the major component)], activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalene; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet and active ingredient, a surfactant is used. Examples of the surfactant are polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkyl arylsulfonates, naphthalenesulfonic acid condensation products, lignin sulfonates and higher alcohol sulfate esters.

Furthermore, to stabilize the dispersion of an active ingredient, tackify it and/or bind it, an adjuvant may be used. Examples of such an adjuvant are casein, gelatin, starch, methylcellulose, carboxymethylcellulose, gum arabic, polyvinyl alcohol, turpentine, bran oil, bentonite and lignin sulfonates.

To improve the flowability of a solid product, an adjuvant may be used. Examples of such an adjuvant are waxes, stearates and alkyl phosphates.

Adjuvants such as naphthalenesulfonic acid condensation products and polycondensates of phosphates may be used as a peptizer for dispersible products.

Adjuvants, e.g. silicon oils may be also used as a defoaming agent.

The content of the active ingredient may be varied as required. In dusts or granules, the suitable content thereof is from 0.01 to 50% by weight. In emulsifiable concentrates, flowable wettable powders, it is also from 0.01 to 50% by weight.

An insecticide containing the hydrazone derivative of the general formula (I) of this invention as an active ingredient is used to control a variety of insect pests in the following manner. That is, it is applied to the insect pests or a site where appearance of growth of the insect pests is undesirable, as it is or after being properly diluted with or suspended in water or the like, in an amount effective to control the insect pests.

The amount of the insecticide containing the hydrazone derivative of the general formula (I) of this invention as an active ingredient is varied depending upon various factors such as a purpose, insect pests to be controlled, a growth state of a plant, tendency of insect pests appearance, weather, environmental conditions, a preparation form, an application method, an application site and an application time. It may be properly chosen in the range of 0.1 g to 5 kg (in terms of the active ingredient) per 10 ares depending upon purposes.

The insecticide containing the hydrazone derivative of the general formula (I) of this invention as an active ingredient may be used in admixture with other insecticides or fungicides in order to expand both spectrum of controllable insect pest species and the period of time when effective applications are possible or to reduce the dosage.

Typical preparation examples and test examples of the present invention are described below but should not be construed as limiting the scope of the invention.

In the preparation examples, parts are all by weight.

Formulation Example 1

| Each compound of the invention | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| Each compound of the invention | 3 parts |
| Clay powder | 82 parts |
| Diatomaceous earth powder | 15 parts |

A dust was prepared by mixing uniformly and grinding the above ingredients.

Formulation Example 3

| Each compound of the invention | 5 parts |
| Mixed powder of benotnite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| Each compound of the invention | 20 parts |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal effect on common cutworm (*Spodoptera litura*)

A piece of cabbage leaf (cultivar: Shikidori) was immersed for about 30 seconds in a liquid chemical prepared by diluting a preparation containing each compound of this invention as an active ingredient to adjust the concentration to 500 ppm. After air-drying, it was placed in a plastic Petri dish having a diameter of 9 cm, and inoculated with second-instar larvae of common cutworm, after which the dish was closed and then allowed to stand in a room thermostated at 25° C. Eight days after the inoculation, the dead and alive were counted. The mortality was calculated according to the following equation and judgement was passed according to the criterion shown below. The test was carried out with triplicate groups of 10 insects.

$$\text{Corrected mortality (\%)} = \frac{\text{Number of dead larvae}}{\text{Number of inoculated larvae}} \times 100$$

Criterion:

| Degree of insecticidal effect | Mortality (%) |
|---|---|
| A | 100 |
| B | 90–90 |
| C | 89–80 |
| D | 79–50 |
| E | Less than 49 |

The results obtained are shown in Table 4.

TABLE 4

| Compound No. | Concentration (ppm) | Judgement | Compound No. | Concentration (ppm) | Judgement |
|---|---|---|---|---|---|
| 3A | 500 | C | 32A | 500 | A |
| 4A | 500 | A | 33A | 500 | A |
| 5A | 500 | A | 34A | 500 | A |
| 7A | 500 | D | 38A | 500 | A |
| 8A | 500 | D | 40A | 500 | A |
| 9A | 500 | A | 41A | 500 | A |
| 10A | 500 | A | 47A | 500 | A |
| 11A | 500 | C | 53A | 500 | A |
| 14A | 500 | A | 54A | 500 | A |
| 17A | 500 | A | 64A | 500 | D |
| 18A | 500 | A | 65A | 500 | C |
| 19A | 500 | A | 73A | 500 | A |
| 20A | 500 | A | 76A | 500 | A |
| 21A | 500 | A | 77A | 500 | A |
| 22A | 500 | A | 78A | 500 | A |
| 23A | 500 | D | 79A | 500 | A |
| 25A | 500 | A | 80A | 500 | A |
| 26A | 500 | A | 81A | 500 | A |
| 27A | 500 | C | 83A | 500 | C |
| 28A | 500 | A | 84A | 500 | A |
| 29A | 500 | A | 87A | 500 | A |
| 30A | 500 | A | 88A | 500 | D |

TABLE 4-continued

| Compound No. | Concentration (ppm) | Judgement | Compound No. | Concentration (ppm) | Judgement |
|---|---|---|---|---|---|
| 31A | 500 | A | 89A | 500 | D |
| 91A | 500 | C | 17B | 500 | A |
| 94A | 500 | D | 18B | 500 | A |
| 95A | 500 | D | 19B | 500 | A |
| 100A | 500 | A | 20B | 500 | D |
| 102A | 500 | D | 21B | 500 | A |
| 103A | 500 | A | 22B | 500 | A |
| 104A | 500 | A | 23B | 500 | A |
| 108A | 500 | A | 25B | 500 | A |
| 110A | 500 | A | 26B | 500 | A |
| 111A | 500 | D | 28B | 500 | A |
| 112A | 500 | A | 30B | 500 | A |
| 113A | 500 | D | 32B | 500 | A |
| 115A | 500 | D | 33B | 500 | A |
| 116A | 500 | A | 34B | 500 | A |
| 3B | 500 | A | 35B | 500 | A |
| 4B | 500 | A | 43B | 500 | A |
| 6B | 500 | C | 44B | 500 | A |
| 7B | 500 | C | 46B | 500 | A |
| 8B | 500 | D | 47B | 500 | C |
| 11B | 500 | A | 48B | 500 | A |
| 12B | 500 | A | 49B | 500 | A |
| 13B | 500 | A | 50B | 500 | A |
| 15B | 500 | A | 51B | 500 | A |
| 16B | 500 | A | 52B | 500 | A |
| 53B | 500 | A | 61B | 500 | A |
| 54B | 500 | A | 62B | 500 | D |
| 55B | 500 | C | 64B | 500 | A |
| 57B | 500 | D | | | |

Test Example 2

Insecticidal effect on adult maize weevil (*Sitophilus zeamais*)

Twenty to thirty grains of the brown rice were immersed for about 30 seconds in a liquid chemical prepared by diluting a preparation containing each compound of this invention as an active ingredient to adjust the concentration to 200 ppm. After air-drying, they were placed in a glass petri dish having a diameter of 4 cm, and inoculated with adult maize weevils, after which the dish was closed and then allowed to stand in a room thermostated at 25° C. Eight days after the inoculation, the dead and alive were counted. The mortality was calculated according to the equation described in Test Example 1 and judgement was passed according to the criterion shown in Test Example 1. The test was carried out with triplicate groups of 10 insects.

The results obtained are in Table 5

TABLE 5

| Compound No. | Concentration (ppm) | Judgement | Compound No. | Concentration (ppm) | Judgement |
|---|---|---|---|---|---|
| 4A | 200 | D | 39A | 200 | A |
| 7A | 200 | B | 40A | 200 | A |
| 8A | 200 | C | 41A | 200 | A |
| 9A | 200 | D | 42A | 200 | A |
| 17A | 200 | B | 43A | 200 | D |
| 18A | 200 | C | 47A | 200 | A |
| 19A | 200 | C | 50A | 200 | B |
| 20A | 200 | C | 53A | 200 | A |
| 21A | 200 | A | 54A | 200 | A |
| 22A | 200 | A | 55A | 200 | A |
| 27A | 200 | D | 56A | 200 | A |
| 28A | 200 | C | 57A | 200 | A |
| 30A | 200 | A | 62A | 200 | D |
| 31A | 200 | D | 63A | 200 | B |
| 38A | 200 | A | 64A | 200 | A |
| 65A | 200 | A | 96A | 200 | A |
| 72A | 200 | C | 97A | 200 | D |
| 73A | 200 | A | 98A | 200 | A |
| 75A | 200 | A | 100A | 200 | A |
| 76A | 200 | A | 101A | 200 | A |
| 77A | 200 | A | 102A | 200 | A |
| 78A | 200 | A | 103A | 200 | A |
| 79A | 200 | A | 104A | 200 | A |
| 80A | 200 | A | 105A | 200 | A |
| 81A | 200 | A | 106A | 200 | A |
| 82A | 200 | A | 107A | 200 | A |
| 83A | 200 | A | 108A | 200 | A |
| 84A | 200 | A | 109A | 200 | A |
| 85A | 200 | A | 110A | 200 | A |
| 86A | 200 | D | 111A | 200 | A |
| 87A | 200 | A | 112A | 200 | A |
| 88A | 200 | A | 113A | 200 | A |
| 89A | 200 | A | 114A | 200 | A |
| 90A | 200 | A | 115A | 200 | A |
| 91A | 200 | A | 116A | 200 | A |
| 92A | 200 | A | 6B | 200 | A |
| 93A | 200 | A | 7B | 200 | D |
| 94A | 200 | A | 11B | 200 | D |
| 95A | 200 | A | 12B | 200 | D |
| 13B | 200 | A | 44B | 200 | A |
| 15B | 200 | A | 45B | 200 | A |
| 16B | 200 | A | 46B | 200 | A |
| 18B | 200 | A | 47B | 200 | A |
| 19B | 200 | A | 48B | 200 | A |
| 21B | 200 | B | 49B | 200 | A |
| 22B | 200 | D | 50B | 200 | A |
| 23B | 200 | A | 51B | 200 | A |
| 28B | 200 | A | 52B | 200 | A |
| 29B | 200 | B | 53B | 200 | A |
| 30B | 200 | A | 54B | 200 | A |
| 31B | 200 | A | 55B | 200 | A |
| 32B | 200 | A | 56B | 200 | A |
| 33B | 200 | A | 57B | 200 | A |
| 34B | 200 | A | 58B | 200 | A |
| 35B | 200 | A | 61B | 200 | A |
| 36B | 200 | A | 62B | 200 | A |
| 37B | 200 | A | 63B | 200 | A |
| 38B | 200 | A | 64B | 200 | A |
| 43B | 200 | A | | | |

What is claimed is:

1. A hydrazone derivative represented by the general formula (I):

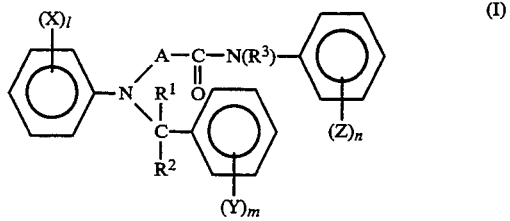

wherein each of $R^1$, $R^2$ and $R^3$ independently represents a hydrogen atom, or an alkyl group having 1 to 5 carbon atoms; A represents —N=C($R^4$)— or —NH—CH($R^4$)— (wherein $R^4$ represents a hydrogen atom or an alkyl group having 1 to 5 carbon atoms); X, which may be the same or different, represents a halogen atom, nitro group, an alkyl group having 1 to 5 carbon atoms, a haloalkyl group having 1 to 5 carbon atoms, an alkoxy group having 1 to 5 carbon atoms, an alkylthio group having 1 to 5 carbon atoms, an alkylsulfinyl group having 1 to 5 carbon atoms, or an alkylsulfonyl group having 1 to 5 carbon atoms; Y, which may be the same or different, represents a halogen atom, nitro group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, an alkylsulfinyl group having 1 to 5 carbon atoms, an alkylsulfonyl group having 1 to 5 carbon atoms, a haloalkylthio group having 1 to 5 carbon atoms, a haloalkylsulfinyl group having 1 to 5 carbon atoms, a haloalkylsulfonyl group having 1 to 5 carbon atoms, an alkynyl group having 2 to 5 carbon atoms, or an alkoxycarbonyl group having 1 to 5 carbon atoms; Z, which may be the same or different, represents a halogen atom, nitro group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, a haloalkylthio group having 1 to 5 carbon atoms, an alkylsulfinyl group having 1 to 5 carbon atoms, a haloalkylsulfinyl group having 1 to 5 carbon atoms, an alkylsulfonyl group having 1 to 5 carbon atoms, a haloalkylsulfonyl group having 1 to 5 carbon atoms, a haloalkylsulfonyloxy group having 1 to 5 carbon atoms, an alkylcarbonyl group having 1 to 5 carbon atoms, or phenoxy group; l, m and n each represents 0 or an integer of 1 to 5.

2. A hydrazone derivative according to claim 1, wherein in the general formula (I), each of $R^1$, $R^2$ and $R^3$ independently represents a hydrogen atom, or an alkyl group having 1 to 5 carbon atoms; A represents —N=C($R^4$)— or —NH—CH($R^4$)— (wherein $R^4$ represents a hydrogen atom, or an alkyl group having 1 to 5 carbon atoms); X, which may be the same or different, represents a halogen atom, an alkyl group having 1 to 5 carbon atoms, or a haloalkyl group having 1 to 5 carbon atoms; Y, which may be the same or different, represents nitro group, an alkyl group having 1 to 5 carbon atoms, a haloalkyl group having 1 to 5 carbon atoms, a haloalkylthio group having 1 to 5 carbon atoms, or a haloalkylsulfinyl group having 1 to 5 carbon atoms; Z, which may be the same or different, represents a halogen atom, nitro group, an alkyl group having 1 to 5 carbon atoms, a haloalkyl group having 1 to 5 carbon atoms, an alkoxy group having 1 to 5 carbon atoms, or a haloalkoxy group having 1 to 5 carbon atoms; l, m and n each represents 0 or an integer of 1 to 3.

3. A hydrazone derivative according to claim 2, wherein in the general formula (I), each of $R^1$, $R^2$ and $R^3$ independently represents a hydrogen atom, or an alkyl group having 1 to 5 carbon atoms; A represents —N=C($R^4$)— or —NH—CH($R^4$)— (wherein $R^4$ represents a hydrogen atom, or an alkyl group having 1 to 5 carbon atoms); X, which may be the same or different, represents a halogen atom, an alkyl group having 1 to 5 carbon atoms, or a haloalkyl group having 1 to 5 carbon atoms; Y, which may be the same or different, represents nitro group, or a haloalkylsulfinyl group having 1 to 5 carbon atoms; Z, which may be the same or different, represents a halogen atom, a haloalkyl group having 1 to 5 carbon atoms, or a haloalkoxy group having 1 to 5 carbon atoms; l, m and n each represents an integer of 1 to 3.

4. A hydrazone derivative according to claim 3, wherein in the general formula (I), at least one X is substituted at the 3-position, at least one Y is substituted at the 4-position, and at least one Z is substituted at the 4-position.

5. An agricultural and horticultural insecticide composition comprising an effective amount of a compound, as active ingredient, a hydrazone derivative represented by the general formula (I):

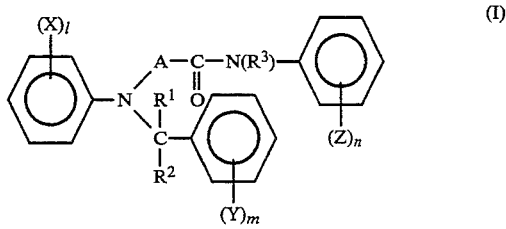

wherein each of $R^1$, $R^2$ and $R^3$ independently represents a hydrogen atom, or an alkyl group having 1 to 5 carbon atoms; A represents —N=C($R^4$)— or —NH—CH($R^4$)— (wherein $R^4$ represents a hydrogen atom, or an alkyl group having 1 to 5 carbon atoms); X, which may be the same or different, represents a halogen atom, nitro group, an alkyl group having 1 to 5 carbon atoms, a haloalkyl group having 1 to 5 carbon atoms, an alkoxy group having 1 to 5 carbon atoms, an alkylthio group having 1 to 5 carbon atoms, an alkylsulfinyl group having 1 to 5 carbon atoms, or an alkylsulfonyl group having 1 to 5 carbon atoms; Y, which may be the same or different, represents a halogen atom, nitro group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, an alkylsulfinyl group having 1 to 5 carbon atoms, an alkylsulfonyl group having 1 to 5 carbon atoms, a haloalkylthio group having 1 to 5 carbon atoms, a haloalkylsulfinyl group having 1 to 5 carbon atoms, a haloalkylsulfonyl group having 1 to 5 carbon atoms, an alkynyl group having 2 to 5 carbon atoms, or an alkoxycarbonyl group having 1 to 5 carbon atoms; Z, which may be the same or different, represents a halogen atom, nitro group, an alkyl group having 1 to 5 carbon atoms, a haloalkyl group having 1 to 5 carbon atoms, an alkoxy group having 1 to 5 carbon atoms, an alkoxy group having 1 to 5 carbon atoms, a haloalkoxy group having 1 to 5 carbon atoms, an alkylthio group having 1 to 5 carbon atoms, a haloalkylthio group having 1 to 5 carbon atoms, an alkylsulfinyl group having 1 to 5 carbon atoms, a haloalkylsulfinyl group having 1 to 5 carbon atoms, an alkylsulfonyl group having 1 to 5 carbon atoms, a haloalkylsulfonyl group having 1 to 5 carbon atoms, a haloalkylsulfonyloxy group having 1 to 5 carbon atoms, an alkylcarbonyl group having 1 to 5 carbon atoms, or phenoxy group; l, m and n each represents 0 or an integer of 1 to 5; and an inert carrier.

6. An agricultural and horticultural insecticide composition according to claim 5 wherein in the general formula (I), each of $R^1$, $R^2$ and $R^3$ independently represents a hydrogen atom, or an alkyl group having 1 to 5 carbon atoms; A represents —N=C($R^4$)— or —NH—CH($R^4$)— (wherein $R^4$ represents a hydrogen atom, or an alkyl group having 1 to 5 carbon atoms); X, which may be the same or different, represents a halogen atom, an alkyl group having 1 to 5 carbon atoms, or a haloalkyl group having 1 to 5 carbon atoms; Y, which may be the same or different, represents nitro group, an alkyl group having 1 to 5 carbon atoms, a haloalkyl group having 1 to 5 carbon atoms, a haloalkylthio group having 1 to 5 carbon atoms, or a haloalkylsulfinyl group having 1 to 5 carbon atoms; Z, which may be the same or different, represents a halogen atom, nitro group, an alkyl group having 1 to 5 carbon atoms, a haloalkyl group having 1 to 5 carbon atoms, an alkoxy group having 1 to 5 carbon atoms, or a haloalkoxy group having 1 to 5 carbon atoms; l, m and n each represents 0 or an integer of 1 to 3.

7. An agricultural and horticultural insecticide composition according to claim 6, wherein in the general formula (I), each of $R^1$, $R^2$ and $R^3$ independently represents a hydrogen atom, or an alkyl group having 1 to 5 carbon atoms; A represents —N═C($R^4$)— or —NH—CH($R^4$)— (wherein $R^4$ represents a hydrogen atom, or an alkyl group having 1 to 5 carbon atoms); X, which may be the same or different, represents a halogen atom, an alkyl group having 1 to 5 carbon atoms, or a haloalkyl group having 1 to 5 carbon atoms; Y, which may be the same or different, represents nitro group, or a haloalkylsulfinyl group having 1 to 5 carbon atoms; Z, which may be the same or different, represents a halogen atom, a haloalkyl group having 1 to 5 carbon atoms, or a haloalkoxy group having 1 to 5 carbon atoms; l, m and n each represents an integer of 1 to 3.

8. An agricultural and horticultural insecticide composition according to claim 7, wherein in the general formula (I), at least one X is substituted at the 3-position, at least one Y is substituted at the 4-position, and at least one Z is substituted at the 4-position.

9. A method for controlling undesirable insect pests which comprises treating useful crops with an agricultural and horticultural insecticide composition comprising an effective amount of a compound, as active ingredient, a hydrazone derivative represented by the general formula (I):

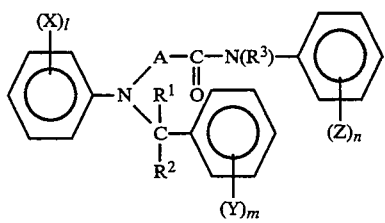

wherein each of $R^1$, $R^2$, and $R^3$ independently represents a hydrogen atom, or an alkyl group having 1 to 5 carbon atoms; A represents —N═C($R^4$)— or —NH—CH($R^4$)— (wherein $R^4$ represents a hydrogen atom, or an alkyl group having 1 to 5 carbon atoms); X, which may be the same or different, represents a halogen atom, nitro group, an alkyl group having 1 to 5 carbon atoms, a haloalkyl group having 1 to 5 carbon atoms, an alkoxy group having 1 to 5 carbon atoms, an alkylthio group having 1 to 5 carbon atoms, an alkylsulfinyl group having 1 to 5 carbon atoms, or an alkylsulfonyl group having 1 to 5 carbon atoms; Y, which may be the same or different, represents a halogen atom, nitro group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, an alkylsulfinyl group having 1 to 5 carbon atoms, an alkylsulfonyl group having 1 to 5 carbon atoms, a haloalkylthio group having 1 to 5 carbon atoms, a haloalkylsulfinyl group having 1 to 5 carbon atoms, a haloalkylsulfonyl group having 1 to 5 carbon atoms, an alkynyl group having 2 to 5 carbon atoms, or an alkoxycarbonyl group having 1 to 5 carbon atoms; Z, which may be the same or different, represents a halogen atom, nitro group, an alkyl group having 1 to 5 carbon atoms, a haloalkyl group having 1 to 5 carbon atoms, an alkoxy group having 1 to 5 carbon atoms, a haloalkoxy group having 1 to 5 carbon atoms, an alkylthio group having 1 to 5 carbon atoms, a haloalkylthio group having 1 to 5 carbon atoms, an alkylsulfinyl group having 1 to 5 carbon atoms, a haloalkylsulfinyl group having 1 to 5 carbon atoms, an alkylsulfonyl group having 1 to 5 carbon atoms, a haloalkylsulfonyl group having 1 to 5 carbon atoms, a haloalkylsulfonyloxy group having 1 to 5 carbon atoms, an alkylcarbonyl group having 1 to 5 carbon atoms, or phenoxy group; l, m and n each represents 0 or an integer of 1 to 5, in the range of 1 g to 5 kg (in terms of the active ingredient) per 10 acres, and an inert carrier, thereby to prevent useful crops from injurous insect pests.

10. A method for controlling according to claim 9, wherein in the general formula (I), each of $R^1$, $R^2$ and $R^3$ independently represents a hydrogen atom, or an alkyl group having 1 to 5 carbon atoms; A represents —N═C($R^4$)— or —NH—CH($R^4$)— (wherein $R^4$ represents a hydrogen atom, or an alkyl group having 1 to 5 carbon atoms); X, which may be the same or different, represents a halogen atom, an alkyl group having 1 to 5 carbon atoms, or a haloalkyl group having 1 to 5 carbon atoms; Y, which may be the same or different, represents nitro group, an alkyl group having 1 to 5 carbon atoms, a haloalkyl group having 1 to 5 carbon atoms, a haloalkylthio group having 1 to 5 carbon atoms, or a haloalkylsulfinyl group having 1 to 5 carbon atoms; Z, which may be the same or different, represents a halogen atom, nitro group, an alkyl group having 1 to 5 carbon atoms, a haloalkyl group having 1 to 5 carbon atoms, an alkoxy group having 1 to 5 carbon atoms, or a haloalkoxy group having 1 to 5 carbon atoms; l, m and n each represents 0 or an integer of 1 to 3.

11. A method for controlling according to claim 10, wherein in the general formula (I), each of $R^1$, $R^2$ and $R^3$ independently represents a hydrogen atom, or an alkyl group having 1 to 5 carbon atoms; A represents —N═C($R^4$)— or —NH—CH($R^4$)— (wherein $R^4$ represents a hydrogen atom, or an alkyl group having 1 to 5 carbon atoms); X, which may be the same or different, represents a halogen atom, an alkyl group having 1 to 5 carbon atoms, or a haloalkyl group having 1 to 5 carbon atoms; Y, which may be the same or different, represents cyano group, nitro group, or a haloalkylsulfinyl group having 1 to 5 carbon atoms; Z, which may be the same or different, represents a halogen atom, a haloalkyl group having 1 to 5 carbon atoms, or a haloalkoxy group having 1 to 5 carbon atoms; l, m and n each represents an integer of 1 to 3.

12. A method for controlling according to claim 11, wherein in the general formula (I), at least one X is substituted at the 3-position, at least one Y is substituted at the 4-position, and at least one Z is substituted at the 4-position.

13. A method for controlling according to claim 12, wherein said insect pests are LEPIDOPTERA or COLEOPTERA.

* * * * *